United States Patent
Zawoy et al.

(10) Patent No.: US 9,056,148 B2
(45) Date of Patent: Jun. 16, 2015

(54) METHOD AND APPARATUS FOR DISINFECTING AND/OR SELF-STERILIZING A STETHOSCOPE USING PLASMA ENERGY

(75) Inventors: Karl R. Zawoy, High Springs, FL (US); Subrata Roy, Gainesville, FL (US); Daniel William Pituch, Nevillewood, PA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 186 days.

(21) Appl. No.: 13/881,767

(22) PCT Filed: Oct. 27, 2011

(86) PCT No.: PCT/US2011/058129
§ 371 (c)(1),
(2), (4) Date: Apr. 26, 2013

(87) PCT Pub. No.: WO2012/058456
PCT Pub. Date: May 3, 2012

(65) Prior Publication Data
US 2013/0218049 A1    Aug. 22, 2013

Related U.S. Application Data (60) Provisional application No. 61/407,226, filed on Oct. 27, 2010.

(51) Int. Cl.
*A61L 2/20* (2006.01)
*A61B 7/02* (2006.01)
*A61L 2/14* (2006.01)

(52) U.S. Cl.
CPC ... *A61L 2/20* (2013.01); *A61B 7/02* (2013.01); *A61L 2/14* (2013.01); *A61B 2562/245* (2013.01); *A61L 2202/24* (2013.01)

(58) Field of Classification Search
CPC ......... A61L 2/20; A61L 2/14; A61L 2202/24; A61B 7/02; A61B 2562/245
See application file for complete search history.

(56) References Cited

U.S. PATENT DOCUMENTS 4,867,268 A    9/1989    Ulert
4,871,046 A    10/1989   Turner
(Continued)

FOREIGN PATENT DOCUMENTS

| | | |
|---|---|---|
| EP | 1477188 A1 | 11/2004 |
| EP | 2030636 A2 | 3/2009 |
| WO | WO-2009/067682 A2 | 5/2009 |

OTHER PUBLICATIONS

Fridman, G., et al., "Bio-Medical Applications of Non-Thermal Atmospheric Pressure Plasma," 37th AIAA Plasma Dynamics and Lasers Conference, Jun. 5-8, 2006.
(Continued)

*Primary Examiner* — Kishor Mayekar
(74) *Attorney, Agent, or Firm* — Saliwanchik, Lloyd & Eisenschenk (57) ABSTRACT

A method and apparatus for disinfecting and/or self-sterilizing at least a portion of the surface of a stethoscope is provided. Methods and devices are provided by which a device or apparatus can generate a sterilizing plasma such that a stethoscope, or portion of a stethoscope, can be placed within or near the device or apparatus so that the plasma disinfects and/or sterilizes and/or decontaminates at least a portion of the stethoscope. A method and apparatus are disclosed for providing a self-disinfecting and/or self-sterilizing and/or self-decontaminating stethoscope and stethoscope disinfecting and/or sterilization apparatus for disinfecting and/or sterilizing, respectively, all or at least a portion of a stethoscope.

19 Claims, 5 Drawing Sheets

(56) References Cited

U.S. PATENT DOCUMENTS

| | | | |
|---|---|---|---|
| 5,225,659 | A | 7/1993 | Kusano et al. |
| 5,641,464 | A | 6/1997 | Briggs, III et al. |
| 5,892,233 | A | 4/1999 | Clement |
| 7,101,518 | B1 | 9/2006 | Ko |
| 7,261,852 | B2 | 8/2007 | Rinzler et al. |
| 7,360,625 | B2 | 4/2008 | Stickley |
| 2002/0175068 | A1 | 11/2002 | Hammerstrom et al. |
| 2005/0236579 | A1 | 10/2005 | Jenkins et al. |
| 2008/0056934 | A1 | 3/2008 | Tsui |
| 2009/0048648 | A1 | 2/2009 | Dacey, Jr. et al. |

OTHER PUBLICATIONS

Fridman, G., et al., "Use of Non-Thermal Atmospheric Pressure Plasma Discharge for Coagulation and Sterilization of Surface Wounds," 32nd IEEE International Conference on Plasma Science, Jun. 20-23, 2005, *IEEE Conference Record Abstracts*, p. 257.

Heise, M., et al., "Sterilization of Polymer Foils with Dielectric Barrier Discharges at Atmospheric Pressure," *Plasmas and Polymers*, 2004, pp. 23-33, vol. 9, No. 1.

Kanazawa, S., et al., "Stable Glow Plasma at Atmospheric Pressure," *Journal of Physics D: Applied Physics*, 1988, pp. 838-840, vol. 21, No. 5.

Kanda, N., et al., "Atmospheric Pressure Glow Plasma and Its Application to Surface Treatment and Film Deposition," *Proceedings of the $10^{th}$ Symposium on Plasma Chemistry*, 1991, vol. 3, Paper No. 3.2-20.

Laroussi, M., et al., "The Resistive Barrier Discharge," *IEEE Transactions on Plasma Science*, 2002, pp. 158-159, vol. 30, No. 1.

Mastanaiah, N., et al., "Inactivation of Yeast Cells Using Dielectric Barrier Discharge," $48^{th}$ *AIAA Aerospace Sciences Meeting and Exhibit*, Jan. 4-7, 2010, Orlando, FL, Doc. No. AIAA-2010-1340.

Moisan, M., et al., "Low-Temperature Sterilization Using Gas Plasmas: A Review of the Experiments and an Analysis of the Inactivation Mechanisms," *International Journal of Pharmaceutics*, 2001, pp. 1-21, vol. 226, Nos. 1-2.

Roth, J.R., "Aerodynamic Flow Acceleration Using Paraelectric and Peristaltic Electrohydrodynamic Effects of a One Atmosphere Uniform Glow Discharge Plasma," *Physics of Plasmas*, 2003, pp. 2117-2126, vol. 10, No. 5.

Roy, S., et al., "Effective Discharge Dynamics for Plasma Actuators," $44^{th}$ AIAA Aerospace Sciences Meeting and Exhibit, Jan. 2006, Reno, NV, Pub No. AIAA-2006-0374.

Roy, S., "Flow Actuation Using Radio Frequency in Partially-Ionized Collisional Plasmas," *Applied Physics Letters*, 2005, Article No. 101502, vol. 86, No. 10.

Schutze, A., et al., "The Atmospheric-Pressure Plasma Jet: A Review and Comparison to Other Plasma Sources," *IEEE Transactions on Plasma Science*, 1998, pp. 1685-1694, vol. 26, No. 6.

Tanino, M., et al., "Sterilization Using Dielectric Barrier Discharge at Atmospheric Pressure," 40th Industry Applications Society Annual Meeting, 2005, Conference Record, pp. 784-788, vol. 2.

Tien, L.C., et al., "ZnO Nanowires for Sensing and Device Applications," 212th Electrochemical Society Meeting, Oct. 7-12, 2007, Abstract No. 1195.

METHOD AND APPARATUS FOR DISINFECTING AND/OR SELF-STERILIZING A STETHOSCOPE USING PLASMA ENERGY

CROSS-REFERENCE TO RELATED APPLICATIONS

This application is the U.S. National Stage Application of International Patent Application No. PCT/US2011/058129, filed Oct. 27, 2011, which claims the benefit of U.S. Provisional Application Ser. No. 61/407,226, filed Oct. 27, 2010, which are both hereby incorporated by reference in their entireties, including all figures, tables and drawings.

BACKGROUND OF INVENTION

It has been estimated that, in the United States, as many as one hospital patient in ten acquires a nosocomial infection, or about 2 million patients a year. Estimates of the annual medical care cost for these infections range from $4.5 billion to $11 billion or more. It is believed that nosocomial infections contributed to approximately 88,000 deaths in the U.S. in 1995. About one third of nosocomial infections are considered preventable. Common nosocomial infections include urinary tract, surgical site, and various pneumonias.

A variety of factors have been determined to contribute to the distribution of nosocomial infections. Of particular concern are handheld medical devices, most notably stethoscopes. Many healthcare practitioners have been concerned that stethoscopes may contribute to the spread of healthcare-associated infections. Nonetheless, healthcare practitioners typically do not take steps to sterilize stethoscopes, even though stethoscopes are often used on multiple patients each day. One reason for this is that current stethoscope designs are difficult to sterilize without risking structural damage. For example, autoclave, thermal, gas, and chemical sterilization methods can damage the diaphragm or other sensitive parts of a stethoscope.

Accordingly, there is a need in the art for a stethoscope and/or stethoscope system that can allow the sterilization of the stethoscope in a safe and efficient manner.

BRIEF SUMMARY

Embodiments of the invention relate to a method and apparatus for disinfecting and/or self-sterilizing at least a portion of the surface of a stethoscope. Specific embodiments provide methods and devices by which a device or apparatus can generate a sterilizing plasma such that a stethoscope, or portion of a stethoscope, can be placed within or near the device or apparatus so that the plasma disinfects and/or sterilizes and/or decontaminates at least a portion of the stethoscope. More specifically, embodiments of the subject invention relate to a method and apparatus for providing a self-disinfecting and/or self-sterilizing and/or self-decontaminating stethoscope and stethoscope disinfecting and/or sterilization apparatus for disinfecting and/or sterilizing, respectively, all or at least a portion of a stethoscope. Specific embodiments of the subject invention successfully address one or more of the above described disadvantages associated with the previously known stethoscope devices and methods, and/or provide certain attributes and advantages that have not been possible with these known devices. In particular, the embodiments of the subject invention provide novel and highly effective methods and devices for convenient and effective disinfecting and/or sterilization of stethoscopes.

Embodiments disclosed herein include a self-sterilizing stethoscope configured with electrodes capable of generating disinfecting and/or self-disinfecting and/or sterilizing plasmas, respectively, across at least some portion of the surface of the stethoscope. In another embodiment, a container or cover is configured with electrodes capable of generating a disinfecting and/or sterilizing plasma field around a stethoscope, or portion of a stethoscope.

Specific embodiments involve the use of electrode pairs driven to create a plasma that generates ozone, where the ozone then disinfects and/or sterilizes a portion of the surface of the stethoscope or other object, where the electrodes are positioned on the surface that is disinfected and/or sterilized, proximate the surface that is disinfected and/or sterilized, or positioned such that ozone produced by the plasma creates by the electrodes is in the environment the surface is exposed to.

Particular embodiments utilize at least two offset, parallel electrodes arranged with a dielectric layer therebetween. More specifically, a ground electrode and a powered electrode are arranged with a dielectric layer therebetween. When sufficient voltage is applied across the electrodes, a plasma field can be generated on the surface of the device proximate the two electrodes.

Figure 4A:
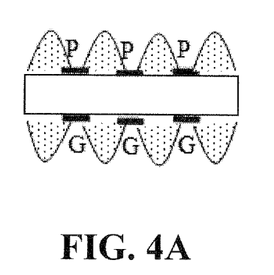
FIGS. 4A-4F show various electrode layouts that can be utilized to create a plasma to disinfect, decontaminate, and/or sterilize a surface.
Figure 4B:
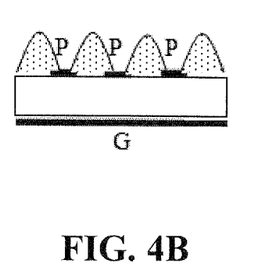
Figure 4C:
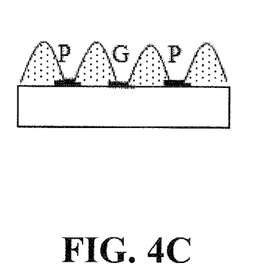
Figure 4D:
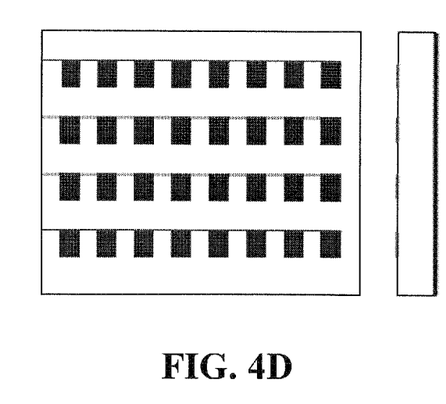
Figure 4E:
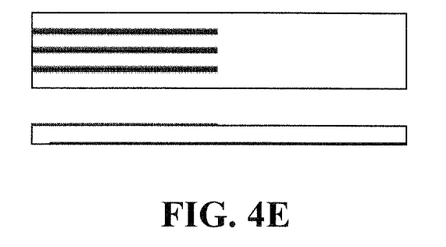
Figure 4F:
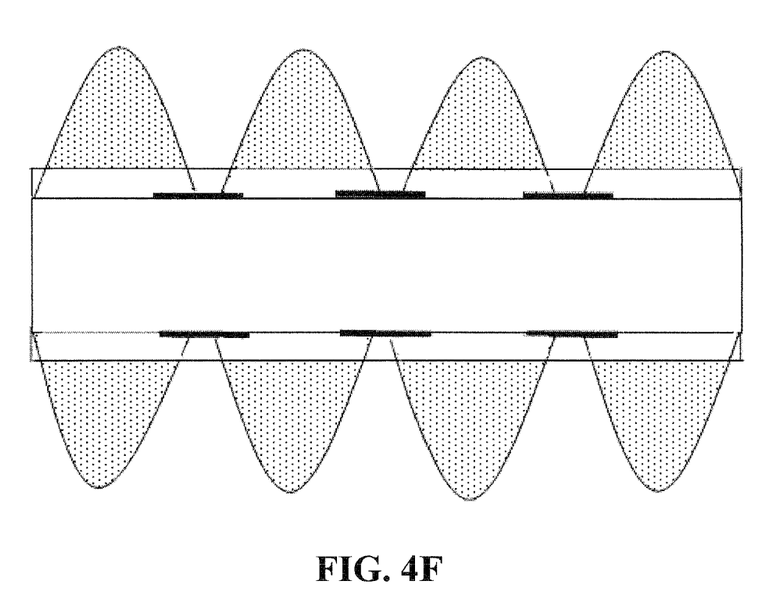

FIGS. 4A-4F show various electrode structures that can be used to disinfect, decontaminate, and/or sterilize a surface. Driving the powered electrodes with a voltage relative to the grounded electrodes produces a plasma that disinfects, decontaminates, and/or sterilizes the active surface and/or other surfaces exposed to the same environment as the plasma is generated. The electrodes can have a variety of shapes and sizes. FIG. 4A shows an electrode pattern where the powered electrodes are separated from the ground electrodes via a layer; while FIGS. 4B and 4C show other electrode configurations that can be used, where FIG. 4B shows the use of a ground plate. Other electrode configurations can also be used. In various embodiments, the electrodes can be exposed to the environment in contact with the surface, the electrodes can be embedded in the surface, the electrodes can have a layer of material, such as a hydrophobic thin insulating layer, Teflon, or a dielectric material layer between the electrode and the environment, or the electrodes can be structured as a combination of exposed, embedded, and covered. FIG. 4F shows an embodiment with a coating over the electrodes such that the electrodes are not exposed to the environment. The outer surface of the coating can then be sterilized via the plasma generated by the electrodes via electric fields penetrating the coating.

Embodiments of the invention can include dielectric barrier discharge (DBD), where a first dielectric coated electrode, or set of electrodes, is exposed at the surface to the surrounding atmosphere (or covered with a coating) and a second electrode, or set of electrodes, is embedded inside a layer of insulator. Where a thin surface coating is in contact with the environment and plasma is generated by electrodes under the surface coating. A voltage can be applied between the first electrode, or set of electrodes, and the second electrode, or set of electrodes, to create a plasma at the surface. In order to disperse the plasma in a continuous fashion over the surface, phase lagged electrode circuitry may be employed. The phase lagged electrode circuitry applies voltages across corresponding electrodes from the first set of electrodes and the second set of electrodes, which form electrode pairs, such that different electrode pairs are excited with voltages having a phase lag compared with the voltage applied to the adjacent electrode pair. In an embodiment, the electrode spacing in each direction is such that the discharge is on both sides of the electrode. One set of electrodes may be powered with a pulsing a.c. or d.c. voltage and the other electrode set can be grounded. For a.c. voltage various waveforms can be utilized, such as sinusoidal, ramp, and sawtooth waveforms. The electrodes may also be operated at a beat frequency. In addition, application of fixed potential (d.c.) can be implemented.

Specific embodiments of electrode structures are shown in FIGS. 4A-4F. The electrode structures shown in FIGS. 4A-4F can also be driven with ac currents. The electrode spacing may vary from a few microns to several mm.

DETAILED DISCLOSURE

Embodiments of the subject invention relate to a method and apparatus for disinfecting and/or sterilizing or decontaminating at least a portion of a stethoscope. In one embodiment, a portable disinfecting and/or sterilization apparatus is provided for inserting and disinfecting and/or sterilizing at least a portion of the stethoscope. In another embodiment, a stethoscope is configured to be self-disinfecting and/or self-sterilizing for at least a portion of the stethoscope. In a specific embodiment, a portable disinfecting device and/or sterilizer is provided that can be used on demand and on location by a healthcare practitioner. Embodiments of the subject disinfecting device and/or sterilizer can be portable or permanently located in an office and/or in proximity to a patient. The disinfecting device and/or sterilizer can have a chamber or orifice wherein a plasma field is generated. An object, such as, for example, a stethoscope, or some portion thereof can be placed within the chamber, such that the plasma field can surround the object and disinfect and/or sterilize the surface of the stethoscope. In a specific example, a stethoscope body and/or diaphragm 13 can be positioned within the chamber. When activated, the portable disinfecting and/or sterilizer chamber can disinfect and/or sterilize, respectively, the surface of the head 12 and/or diaphragm 13 of the stethoscope 10.

Another embodiment utilizes a cover or sleeve that can generate a plasma field, in which a stethoscope or portion of a stethoscope can be encased for disinfecting and/or sterilization and/or decontamination. The cover can be kept on during use or the cover can be removed during use and then placed on the head 12 and diaphragm 13 and/or other portions of the stethoscope in order to disinfect and/or sterilize the covered portions.

Another embodiment provides a stethoscope that, when activated, generates its own plasma field allowing it to effectively self-disinfect and/or self-sterilize, and/or decontaminate all or portion of itself. With this embodiment, a stethoscope can be positioned on an inert or isolated surface, or held away from human contact, for a period of time to allow disinfecting and/or sterilization and/or decontamination. The stethoscope can have a head and diaphragm that self-disinfects and/or self-sterilizes and/or other portions of the stethoscope that self-disinfect and/or self-sterilize.

Figures 1A, 1B:
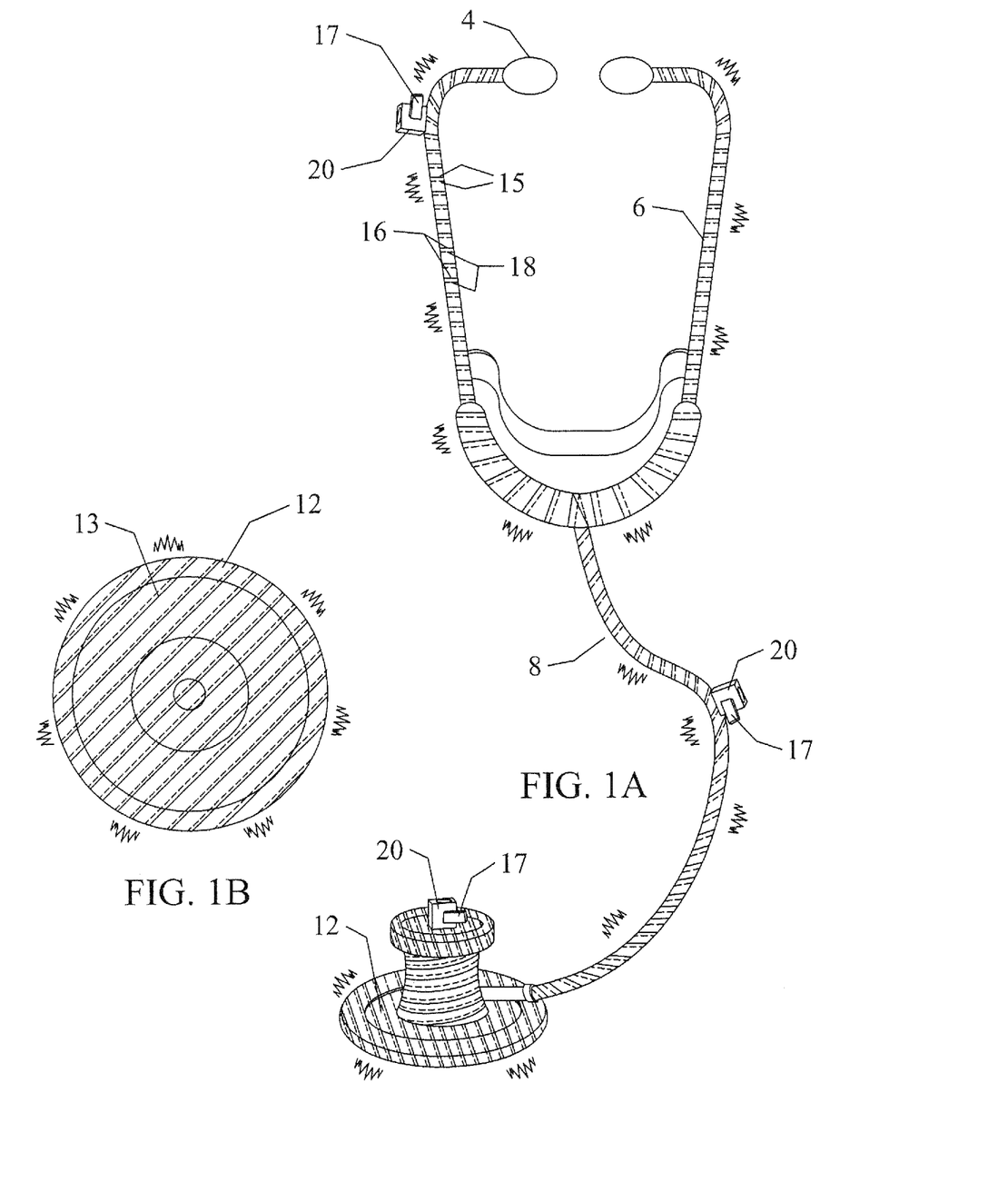
FIGS. 1A-1B show a self-disinfecting and/or self-sterilizing stethoscope in accordance with an embodiment of the subject invention, where the parallel lines represent parallel electrodes, with the solid lines representing a first electrode on the surface of the device and the dotted lines representing a second electrode below the surface of the device and separated from the first electrode by a dielectric material.

Regarding a stethoscope that can generate a plasma field that can disinfect and/or sterilize all or some portion of the stethoscope surface by placing the stethoscope on an inert or isolated surface, or moving the stethoscope away from human contact, for a period of time to allow disinfecting and/or sterilization, reference is made to FIGS. 1A and 1B.

FIGS. 1A and 1B show an embodiment of a self-disinfecting and/or self-sterilizing stethoscope 10 that includes a headset 11 with at least one, more particularly two, ear tips 4 leading to at least one, more particularly two ear tubes 6. The ear tubes 6 lead to a stem 8, which is connected to diaphragm 13 and diaphragm head 12. The diaphragm head 12, which holds the diaphragm 13, is attached to the stem 8.

In the embodiment shown in FIGS. 1A and 1B, the stethoscope headset 11 and ear tubes 6 have incorporated therein two or more pairs of plasma generating electrodes 15 where first electrode wire 16 at or near the surface of the stethoscope, and a second, electrode wire 18 positioned below the first electrode wire, are arranged with a dielectric barrier therebetween. Either the first electrode 16 or the second electrode 18 can act as a ground, if desired. Both electrode wires are wound spirally in the same direction around the ear tubes, as shown in FIG. 1A. In this embodiment, the electrodes are generally parallel, but offset. In other words, the first electrode is not directly above the second electrode, as seen in FIGS. 1A and 1B. Other electrode structures, rather than the spiral structure shown in FIG. 1A, can be utilized, so long as the electrode structure provides sufficient coverage of the surface with disinfecting and/or sterilizing and/or decontaminating plasma when powered. In a further embodiment, one or more electrical connectors 20 can be operably connected to the first electrode 16 and the second electrode 18. The electrical connector 20 can subsequently be operably connectable to an electrical source, such as a wall plug or outlet or similar device to provide an appropriate voltage input to the first and second electrodes. Although three electrical connectors 20 are shown in FIG. 1, a stethoscope can have just one electrical connector 20, which can be located at a convenient location and allow disinfecting and/or sterilization and/or decontamination of all or a portion of the stethoscope. In a specific embodiment, more than one electrical connector can be utilized with each electrical connector facilitating the disinfecting and/or sterilization of a section of the stethoscope.

Figure 3:
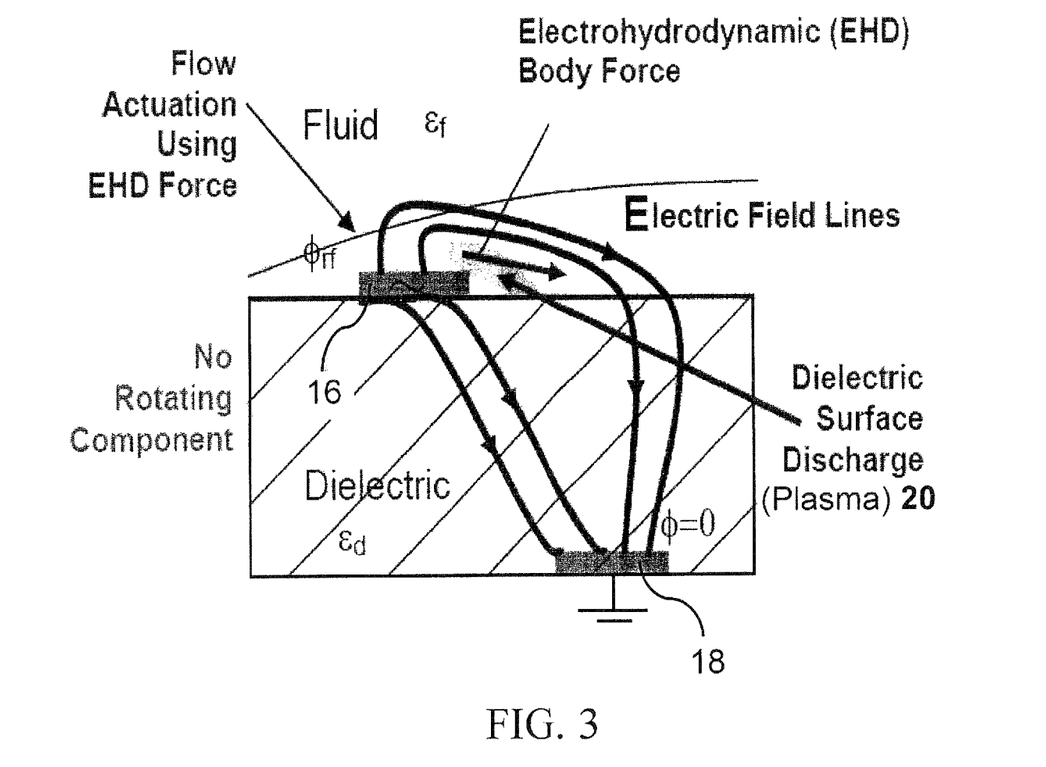
FIG. 3 shows a dielectric surface discharge in accordance with an embodiment of the invention.

When the electrical connector 20 is operably connected to a plug or other source of electricity, voltage applied across the first electrode 16 and the second electrode 18 will cause an electric field through the dielectric layer from the first electrode 16 to the second electrode 18. However, as shown in FIG. 3, due to known electrohydrodynamic forces, the electric field lines will flow over the dielectric surface creating a surface discharge or plasma field 20 on the surface of the dielectric layer, before flowing through the dielectric layer to the second electrode. The intense heat of the plasma field generated on the surface of the dielectric layer can disinfect and/or sterilize and/or decontaminate that portion of the dielectric surface with which it comes into contact.

In one embodiment, the headset 11 of a stethoscope is configured with a first electrode 16 and a second electrode 18, such that the entire surface of the headset can be disinfected and/or sterilized when voltage is applied across the first and second electrodes. A voltage can be applied anywhere along the electrode. In one embodiment, voltage is applied at or near one ear tip 4 so that the voltage is applied via the electrode pair all the way to the second ear tip. The electrodes can branch and also down the stem 8, such that the voltage can be applied down the stem 8 and to the diaphragm head and diaphragm. Accordingly, applying a voltage to a single electrical connector 20 can disinfect and/or sterilize the entire stethoscope, or portion thereof.

In another embodiment, one or more additional sections of a stethoscope are configured with electrodes. In a specific embodiment, the entire surface of a stethoscope is configured with a series of electrode pairs. In this embodiment, the electrode pairs can be wound around or otherwise arranged throughout the surface of the stethoscope such that each electrical connector 20 provides voltage to a portion of the stethoscope. This can provide a convenient method for disinfecting and/or sterilizing an entire stethoscope, or a commonly touched portion of a stethoscope, between patient visits.

FIG. 1A shows an embodiment where the electrodes are configured, such that more than one electrical connector is required to disinfect and/or sterilize the entire stethoscope. FIG. 1A shows an embodiment where the headset 11, stem 8, and stethoscope head 12, including the diaphragm 13, are all provided with separate electrical connectors 20. One advantage to using multiple electrical connectors is that certain portions of the stethoscope can be disinfected and/or sterilized on a more regular basis. For example, the stethoscope head 12 and diaphragm 13 can be configured with a single set of electrodes that are electrically isolated from electrodes in other parts of the stethoscope. With this embodiment, the stethoscope head and diaphragm can be simultaneously disinfected and/or sterilized after used with patient. Since the stethoscope head electrodes are isolated from the rest of the stethoscope, the stethoscope head could be disinfected and/or sterilized without having to remove it from the physician. This can provide a quick, easy way for at least some portion of a stethoscope to be disinfected and/or sterilized between patients.

A person with skill in the art and having benefit of the subject disclosure would be able to determine any of a variety of configurations of plasma generating electrodes and/or electrical connectors for disinfecting and/or sterilizing all or part of a stethoscope. It is contemplated that such alternatives are within the scope of the subject invention.

In some circumstances, such as field or clinic use, it is not always possible or feasible to utilize or access built-in electrical power supplies through electrical connectors between each patient. In such situations, it can be more advantageous for the plasma generating electrodes 15 to be connected or connectable to a more portable power source. In one embodiment, the plasma generating electrodes 15 are operably connected or connectable to a battery or other self-contained power supply. In a more specific embodiment, a stethoscope configured with one or more pairs of plasma generating electrodes has a self-contained battery or other power supply. In a further embodiment, the plasma generating electrodes and/or the self-contained power supply have a control mechanism 17, such as for example an on/off switch, which can control the flow of electricity through the electrodes. With this embodiment, the healthcare practitioner can activate the control mechanism, e.g., push a button on the stethoscope, or otherwise trigger the plasma disinfecting and/or plasma sterilization on the active surface of the stethoscope.

The sterilization and/or decontamination of embodiments of the subject stethoscope can reduce or eliminate, for example, pathogens, bacteria, chemical agents, biological agents, or other materials. The plasma can change the chemical structure and can gasify materials on the surface of the stethoscope.

In specific embodiments of the invention, surfaces can be sterilized in accordance with appropriate International Organization for Sterilization (ISO) standards. Examples of ISO standards that can be met by embodiments of the subject invention include, but are not limited to, ISO 17665:2004—Sterilization of medical devices—Information to be provided by the manufacturer for the processing of resterilizable medical devices, ISO 11138-4:2006-Sterilization of health care products—Biological indicators, ISO 11737-2:1998—Sterilization of medical devices—Microbiological methods—Part 2: Tests of sterility performed in the validation of a sterilization process, ISO 14161:2000—Sterilization of health care products—Biological indicators—Guidance for the selection, use and interpretation of results, ISO 14937:2000—Sterilization of health care products—General requirements for characterization of a sterilizing agent and the development, validation and routine control of a sterilization process for medical devices, ISO 11737-1:2006—Sterilization of medical devices—Microbiological methods—Part 1: Determination of a population of microorganisms on products. In addition, various embodiments can meet the standards provided in Seymour S. Block. 2000 Disinfection, Sterilization, and Preservation $5^{th}$ ed. Lippencott, Williams, and Wilkens.

The disinfecting of embodiments of the subject stethoscope can accomplish one or more of the following: reduce infectious agents and microbial contamination; eliminate many or all pathogenic microorganisms, with the possible exception of bacterial spores; and kill mycobacteria, vegetative bacteria, most viruses, and most fungi. Disinfecting, without sterilization, can be accomplished by exposing the surface of at least a portion of the surface of the stethoscope to a plasma generated at a lower power level than used for sterilization and/or exposing the surface for a shorter duration than used for sterilization. A reduced power level can allow the disinfecting apparatus to be produced for a lower cost and a reduced exposure time can allow the disinfecting apparatus to be operated at a lower cost and allow the disinfecting to be accomplished quicker, thereby saving costs and potentially increasing compliance with rules regarding disinfecting the at least a portion of the stethoscope. In this way, in a specific embodiment, a stethoscope can allow disinfecting of at least a portion of the stethoscope by operating the plasma generation apparatus, either built into the stethoscope or external to the stethoscope, to be operated at a first power level and/or for a first duration to disinfect the at least a portion of the stethoscope, and to be operated at a second power level and/or for a second duration to sterilize the at least a portion of the stethoscope. In this way, in a specific embodiment, where sterilization of at least a portion of the stethoscope via a plasma may take 20-30 minutes, disinfecting the at last a portion of the stethoscope via the plasma may take much less time, for example 2-3 minutes.

Further specific embodiments can disinfect at least a portion of the subject stethoscope to one of three levels of disinfection, namely high, intermediate, and low, as defined by the U.S. Center for Disease Control (CDC). High-level disinfection kills all organisms, except high levels of bacterial spores. Intermediate-level disinfection kills mycobacteria, most viruses, and bacteria. Low-level disinfection kills some viruses and bacteria. Specific embodiments can disinfect to a single level, namely high, intermediate, or low. Other embodiments can disinfect to either of two levels, or any of three levels, where the user can select the desired level of disinfection.

Figure 2:
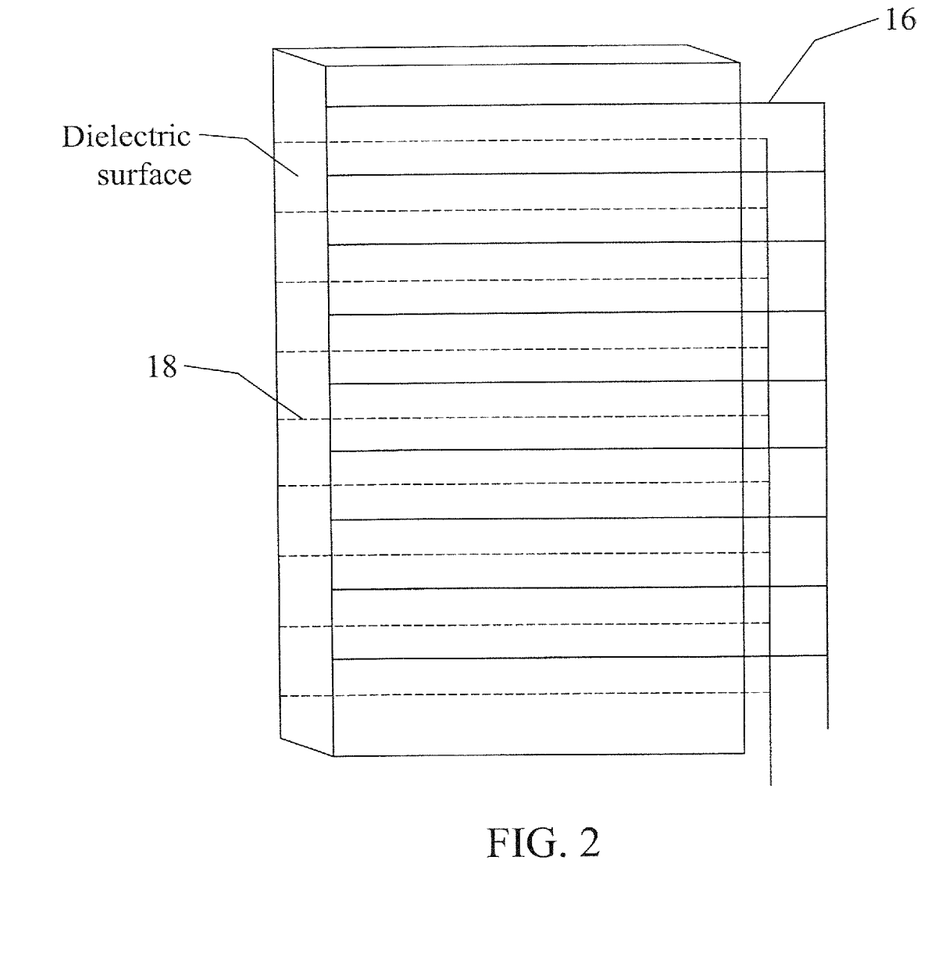
FIG. 2 shows a embodiment of an electrode arrangement according to the subject invention, where a first electrode is positioned on or near the surface of a layer of dielectric material and a second electrode is parallel to, but offset from and below, the first electrode, so that the dielectric material separates the first and second electrodes.

In a specific embodiment, a voltage between 2-20 kV can be applied across electrodes. In another specific embodiment, a peak-to-peak ac voltage of 2-20 kV can be applied, and in a more specific embodiment the ac voltage is 1-50 kHz RF voltage. FIGS. 1A-B show an embodiment of a self-sterilizing stethoscope, with FIG. 1A showing the entire stethoscope and FIG. 1B showing the diaphragm surface that is exposed to the patient in order to take a reading with the stethoscope. In an embodiment, all exterior surfaces of the stethoscope are sterilized. In another embodiment, components of the stethoscope are sterilized, such as the exposed surface of the diaphragm, diaphragm head, and/or stem. The surface can have a dielectric layer positioned in between two electrode layers. Referring to FIG. 2, a layer of ground electrodes are positioned apart from a layer of powered electrodes. FIG. 3 shows an end cross-sectional view of the electrode structure shown in FIG. 2. In a specific embodiment, a ground plane can be used rather than the electrodes separated from the electrodes near the surface by the dielectric material. Driving the powered electrodes with a voltage relative to the grounded electrodes produces a plasma that disinfects and/or sterilizes and/or decontaminates the active surface, wherein the active surface is the surface, or at least a portion of the surface, that needs to be disinfected and/or sterilized. The electrodes can have a variety of shapes and sizes. Other electrode configurations can also be used. In various embodiments, the electrodes can be exposed to the environment in contact with the surface, the electrodes can be embedded in the surface, the electrodes can have a layer of material, such as hydrophobic thin insulating layer, Teflon, or a dielectric material layer between the electrode and the environment, or the electrodes can be structured as a combination of exposed, embedded, and covered. The outer surface of the coating can then be disinfected and/or sterilized via the plasma generated by the electrodes via electric fields penetrating the coating.

Other electrode structures can be utilized as well. The tube 8 can have a plastic layer with wire electrodes braided around the outside of the tube so as to leave spaces between the wire electrodes or otherwise prevent contact of adjacent wire electrodes. With one braid, the cross-hatching wire electrodes can be opposite electrodes. Some wire electrodes can be dielectrics to keep metal electrodes from touching. Again, a variety of electrode configurations and/or shapes can be used with the tube 8.

FIG. 2 shows an electrode structure on a surface that can be utilized on a surface of a chamber or other enclosure for disinfecting, sterilizing, and/or decontaminating a stethoscope or other object, or a portion thereof. An embodiment of the invention relates to such an enclosure. In a specific embodiment, the enclosure opens to allow placement of a stethoscope or other object, or portion thereof, and closes to allow isolation of the stethoscope or other object, or portion thereof, from the environment outside of the enclosure. In this way ozone produced within the enclosure during the disinfecting, sterilization, and/or decontaminating of the stethoscope or other object does not leak out into the environment. In a further specific embodiment, the gaseous environment within the enclosure is filtered, or otherwise processed, to remove or reduce the ozone produced via the electrodes during disinfecting, sterilization, and/or decontamination, prior to opening the enclosure to remove the stethoscope or other object.

In a preferred embodiment utilizing an enclosure to disinfect, sterilize, and/or decontaminate a stethoscope or other object, or portion thereof, an internal surface within the enclosure can have a contour that is complimentary to the shape of the stethoscope or other object such that the volume of the internal environment can be kept small in order to increase the concentration of ozone in the internal environment. In specific embodiments, the ratio of the square area, in $cm^2$, used to create plasma to volume, in $cm^3$, within the enclosure that ozone produced by the electrodes can diffuse is at or above a certain value, such as 0.8, 0.9, 1.0, 1.1, 1.2, 1.3, 1.4, or 1.5, in order that the concentration of ozone within such volume is at least a certain level. In another embodiment, the ratio of the square area of the internal surfaces of the enclosure exposed to the internal environment of the enclosure to the volume of the internal environment of the enclosure is at least a certain level, such as 0.8, 0.9, 1.0, 1.1, 1.2, 1.3, 1.4, or 1.5, in order that the concentration of ozone within such volume is at least a certain level. In this way, the stethoscope or other object in the enclosure is exposed to the ozone in the internal environment such that the ozone can assist in the disinfecting, sterilization, and/or decontamination of the stethoscope or other object. In an embodiment, the stethoscope or other object would not have any circuitry or electrodes for creating the plasma, but, rather, the enclosure incorporates the electrodes and, optionally, the circuitry. In another embodiment, the stethoscope or other object incorporates the electrodes to create the plasma, and, optionally, the appropriate circuitry, and is still placed in the enclosure for a portion or all of the disinfecting, sterilization, and/or decontamination process. In this way, the ozone created can assist with disinfecting, sterilization, and/or decontamination.

In a further embodiment, circuitry external to the stethoscope or other object can inductively power the electrodes incorporated into the stethoscope or other object and the stethoscope or other object can optionally be placed in the enclosure during at least a portion of the disinfecting, sterilizing, and/or decontaminating process. In an embodiment, the circuitry external to the stethoscope or other object can include one or more transmit coils that produce a charging magnetic field and the system can include one or more receive coils that produce a voltage and/or current when exposed to the transmit magnetic field so as to provide power for the electrodes positioned on the stethoscope or other object. The receiver coil(s) can be incorporated with the stethoscope or other object or can be external to the stethoscope or other object and electrically connected to the stethoscope or other object to drive the electrodes on the stethoscope or other object.

Specific embodiments can include a power source incorporated with the stethoscope or other object. Alternative embodiments can utilize a power source external to the stethoscope or other object and have optional connectors to releasably connect to the power source.

As discussed above, the generation of the plasma via the electrodes can also produce ozone. Further, UV radiation can be produced by the electrodes, as can ionized air resulting from breaking up of $O_2$ and other gases into plasma field and a combination of ions. Exposure of the surface of the stethoscope or other object to one or more of: the ozone, UV radiation, ionized air, and/or combination of ions, produced by the electrodes can enhance the disinfecting, sterilization, and/or decontamination, and/or disinfect, sterilize, and/or decontaminate, such surface. Placing the stethoscope or other object in an enclosure, as discussed above, can enhance the effects of such one or more of ozone, UV radiation, ionized air, and/or combination of ions. In a specific embodiment, one or more surface not directly exposed to the plasma generated by the electrodes can be at least partially disinfected, sterilized, and/or decontaminated by exposure of the same surface to one or more of the ozone, UV radiation, ionized air, and/or combination of ions produced by the electrodes, when the stethoscope or other object is placed in the enclosure, such that placement in the enclosure causes the concentration of the one or more ozone, UV, and ions to be high enough to disinfect, sterilize, and/or decontaminate the surface, even if the surface is not exposed to the plasma generated by the electrodes.

In further specific embodiments, sensing technology can be incorporated into the stethoscope or other object. In this way, the stethoscope or other object can detect when a certain state or event has occurred in order to initiate disinfecting, sterilization, and/or decontamination. In an embodiment, the stethoscope or other object can be hung up in a certain position or in one of a number of positions, for example upside-down, and upon detection of the same the electrodes can be triggered to produce plasma. Other states or events that can be detected and trigger disinfecting, sterilization, and/or decontamination include, but are not limited to, detection of when the stethoscope or other object is within a certain distance of a particular location or is within a certain area or volume, when the stethoscope or other object is not moving or has not moved for a certain time period, and/or when the stethoscope or other object has experienced a certain length of time since the last disinfecting, sterilization, and/or decontamination. In a specific embodiment, upon triggering by such sensors, the electrodes can be driven so as not to fully sterilize, but to only decontaminate, or only to disinfect, where such limited decontamination may be safer and may result from a lower voltage and/or current, and/or shorter or pulsed drive times. In this way, the stethoscope or other object may be disinfected without a full sterilization. Each of the embodiments disclosed in the subject disclosure can be operated so as to disinfect a surface without decontaminating or sterilizing the surface, and can be operated to disinfect a surface without sterilizing the surface. Such control of the disinfecting process can be accomplished by one or more of the following: operating at a lower operating voltage and/or for a shorter operating period of time; keeping the concentration of ozone created by the plasma the surface is exposed to below a certain threshold and/or limiting the time of exposure of the surface to the ozone; and keeping the amount of UV radiation, concentration of ions and ionized air below certain thresholds and/or limiting the time of exposure of the surface to the same.

Specific embodiments can involve maintaining the ozone produced by the plasma in the volume within the enclosure that the surface to be disinfected, decontaminated, and/or sterilized is in contact with such that the wavelength of the LTV created by the plasma changes to a wavelength more effective for disinfecting, decontaminating, and/or sterilizing the surface. In this way, the UV radiation can be more effective at destroying the cell's DNA and preventing the cell from reproducing.

Further specific embodiments can break the surface of the stethoscope or other object, or internal surface of the enclosure proximate the stethoscope or other object when enclosed in the enclosure, can be broken into regions. In this way, the electrodes of the regions can be driven such that not al of the regions are powered at once. For at least a portion of the disinfecting, sterilize, and/or decontamination cycle, one or more regions an use the corresponding electrodes for sensing while other regions are being driven to generate plasma, regions can be driven sequentially in accordance with a certain schedule (multiplexing and/or rasterizing), zones with more contamination are driven more, or other purposes for driving less than all of the regions at the same time. In this way, in an embodiment with four zones, zone one can be powered while zones two, three, and/or four are sensed, and/or one zone at a time can be powered, zones are powered in accordance with a schedule.

Specific embodiments can incorporate electrodes on at least a portion of the stethoscope or other object and can connect the stethoscope or other object to a power source when disinfecting, sterilizing, and/or decontamination is needed or desired.

NUMBERED EMBODIMENTS

1. A system, comprising:
   an enclosure;
   an object;
   one or more first electrodes;
   one or more second electrodes; and
   a voltage supply,
   wherein when at least a portion of the object is positioned within the enclosure and the enclosure is closed, such that the at least a portion of the object is exposed to an internal environment within the enclosure and the internal environment is separate from an external environment in which the enclosure is positioned, and the voltage supply supplies a voltage across at least one of the one or more first electrodes and at least one of the one or more second electrodes such that a plasma is generated, at least a portion of the object is disinfected, decontaminated, and/or sterilized.
2. The system according to embodiment 1, wherein the at least a portion of the object is disinfected.
3. The system according to embodiment 2, wherein the at least a portion of the object is not sterilized.
4. The system according to embodiment 1,
   wherein the one or more first electrodes and the one or more second electrodes are proximate the at least a portion of the surface of the object.
5. The system according to embodiment 1, wherein the one or more first electrodes and the one or more second electrodes are proximate an internal surface of the enclosure.
6. The system according to embodiment 4, wherein the plasma disinfects, decontaminates, and/or sterilizes the at least a portion of the surface of the object.
7. The system according to embodiment 5, wherein the plasma disinfects, decontaminates, and/or sterilizes the at least a portion of the surface of the object.
8. The system according to embodiment 4, wherein ozone created by the plasma disinfects, decontaminates, and/or sterilizes the at least a portion of the surface of the object.
9. The system according to embodiment 5, wherein ozone created by the plasma disinfects, decontaminates, and/or sterilizes the at least a portion of the surface of the object.
10. The system according to embodiment 1, wherein all of the surface of the object exposed to the internal environment is disinfected, decontaminated, and/or sterilized.
11. The system according to embodiment 1, wherein the object is a stethoscope.
2. The system according to embodiment 3, wherein the object is a stethoscope.
13. The system according to embodiment 12, wherein the plasma disinfects the at least a portion of the surface.
14. The system according to embodiment 12, wherein ozone created by the plasma disinfects the at least a portion of the surface.
15. The system according to embodiment 11, wherein the at least a portion of the surface of the object comprises an exterior surface of a diaphragm of the stethoscope.

16. The system according to embodiment 1, wherein a ratio of an area of the at least a portion of the surface of the object in $cm^3$ to a volume of the internal environment in $cm^3$ is at least 1.

17. The system according to embodiment 10, wherein when the object is positioned within the enclosure ozone created by the plasma is prevented from leaking from the internal environment to the external environment.

18. The system according to embodiment 9, wherein when the object is positioned within the enclosure ozone created by the plasma is prevented from leaking from the internal environment to the external environment.

19. The system according to embodiment 8, further comprising:
a filter subsystem, wherein the filter subsystem filters ozone from the internal environment after the plasma creates the ozone and before the enclosure is opened.

20. The system according to embodiment 9, further comprising:
a filter subsystem, wherein the filter subsystem filters ozone from the internal environment after the plasma creates the ozone and before the enclosure is opened.

21. The system according to embodiment 1, wherein an internal surface of the enclosure has a contour that is complementary to a portion of the at least a portion of the surface of the object.

22. The system according to embodiment 5, wherein the internal surface of the enclosure has a contour that is complementary to a portion of the at least a portion of the surface of the object.

23. The system according to embodiment 1, wherein the voltage supply supplies the voltage across the at least one of the one or more first electrodes and the at least one or more second electrodes via inductive coupling.

24. The system according to embodiment 1, further comprising:
one or more sensors, wherein when the one or more sensors detects one of at least one event or state, supplying the voltage is triggered.

25. The system according to embodiment 1, wherein the at least a portion of the surface of the object is divided into a plurality of regions, wherein the voltage source supplies the voltage such that the plurality of regions are sequentially disinfected, decontaminated, or sterilized.

26. The system according to embodiment 1, wherein the at least a portion of the surface of the object is divided into a plurality of regions, wherein the voltage source supplies the voltage such that the plurality of regions are each disinfected, decontaminated, or sterilized during a corresponding first plurality of periods of time and monitored via a corresponding plurality of sensors during a corresponding second plurality of periods of time, wherein each period of time of the first plurality of periods of time does not overlay with each corresponding period of time of the second plurality of periods of time.

27. The system according to embodiment 1, wherein UV radiation created by the plasma disinfects, decontaminates, and/or sterilizes the at least a portion of the surface of the object.

28. The system according to embodiment 27, wherein the UV radiation disinfects the at least a portion of the surface of the object, wherein the UV radiation does not sterilize at least a portion of the surface of the object.

29. The system according to embodiment 1, wherein ionized air and/or ions created by the plasma disinfects, decontaminates, and/or sterilizes the at least a portion of the surface of the object.

30. The system according to embodiment 29, wherein the ionized air and/or ions disinfects the at least a portion of the surface of the object, wherein the UV radiation does not sterilize at least a portion of the surface of the object.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

[1] Kanda, N., M. Kogoma, H. Jinno, H. Uchiyama and S. Okazaki, Proc. 10th Symp. On Plasma Chem., Vol. 3, Paper no. 3.2-20 (1991).
[2] Roth, J. R., Physics of Plasmas, 10 (5), 2117 (2003).
[3] S. Roy, K. P. Singh, H. Kumar, D. Gaitonde, and M. Visbal, Effective discharge dynamics for plasma actuators, AIAA-2006-0374, 44th Aerospace Sciences Meeting and Exhibit, 9-12 Jan. 2006.
[4] S. Roy, Flow actuation using radio frequency in partially-ionized collisional plasmas, Applied Physics Letters, 86 (10) 101502 (2005).
[5] M. Heisel, W. Neffl, O. Franken, P. Muranyi and J. Wunderlich, Sterilization of Polymer Foils with Dielectric Barrier Discharges at Atmospheric Pressure, Plasmas and Polymers, 9 (1) 23-33 (2004).
[6] M. Tanino, W. Xilu, K. Takashima, S. Katsura and A. Mizuno, Sterilization using dielectric barrier discharge at atmospheric pressure, Industry Applications Conference, 2005. Fortieth IAS Annual Meeting. Vol. 2, 784-788 (2005).
[7] M. Moisan, J. Barbeau, S. Moreau, J. Pelletier, M. Tabrizian and L'H. Yahia, Low-temperature sterilization using gas plasmas: a review of the experiments and an analysis of the inactivation mechanisms, International Journal of Pharmaceutics, 226, 1-21 (2001).
[8] Fridman G., Peddinghaus L., Vinovrski T., Jah A., Fridman A., Balasubramanian M., Gutsol A., Friedman G., "Use of Non-Thermal Atmospheric Pressure Plasma Discharge for Coagulation and Sterilization of Surface Wounds", 32nd IEEE International Conference on Plasma Science, Jun. 20-23, 2005, Monterey, Calif., IEEE Conference Record—Abstracts, p. 257.
[9] G. Fridman, A. Shereshevsky, M. Peddinghaus, A. Gutsol, V. Vasilets, A. Brooks, M. Balasubramanian, G. Friedman, and A. Fridman, Drexel University, Philadelphia, Pa. "Bio-Medical Applications of Non-Thermal Atmospheric Pressure Plasma" AIAA-2006-2902 37th AIAA Plasma dynamics and Lasers Conference, San Francisco, Calif., Jun. 5-8, 2006.
[10] Andrew Rinzler, et al., "Transparent electrodes from single wall carbon nanotubes." U.S. Pat. No. 7,261,852. 28 Aug. 2007.
[11] F. Ren, ZnO Nanowires for Sensing and Device Applications, $212^{th}$ ECS Meeting, Oct. 7-12, 2007, Washington, D.C.
[12] S. Kanazawa, M. Kogoma, T. Moriwaki, and S. Okazaki, J. Appl. Phys. D: Appl. Phys. 21 (1988) 838.
[13] M. Laroussi, I. Alexeff, J. P. Richardson, and F. F. Dyer, IEEE Trans. Plasma Sci. 30 (2002) 158.

[14] A. Scutze, J. Y. Jeong, S. E. Babyan, J. park, G. S. Selwyn, and R. F. Hicks, *IEEE Trans. Plasma Sci.* 26 (1998) 1685.

What is claimed is:

1. A stethoscope, comprising:
    a diaphragm having an exposed exterior surface of the diaphragm, wherein the exposed exterior surface of the diaphragm is adapted to be positioned on or near a patient to vibrate in response to movement generated by the patient;
    a pair of electrodes comprising a first electrode and a second electrode, wherein a diaphragm portion of each electrode of the pair of electrodes is positioned on, in, and/or near the diaphragm; and
    a dielectric material, wherein the dielectric material is positioned between the diaphragm portion of the first electrode and the diaphragm portion of the second electrode,
    wherein when a first voltage potential is applied across the pair of electrodes for a first period of time a plasma discharge is generated proximate the exposed exterior surface of the diaphragm such that the plasma disinfects the exposed exterior surface of the diaphragm.

2. The stethoscope according to claim 1, wherein the diaphragm comprises the dielectric material and the diaphragm portion of the first electrode is positioned on or near the exposed exterior surface of the diaphragm.

3. The stethoscope according to claim 1, wherein the diaphragm portion of each electrode of the pair of electrodes comprises a plurality of parallel structures extending in a common plane.

4. The stethoscope according to claim 1, wherein the common plane of the diaphragm portion of the first electrode is arranged substantially parallel to the common plane of the diaphragm portion of the second electrode.

5. The stethoscope according to claim 4, wherein the parallel structures of the diaphragm portion of the first electrode are arranged substantially parallel to the parallel structures of the diaphragm portion of the second electrode.

6. The stethoscope according to claim 1, further comprising:
    a diaphragm head, wherein the diaphragm head houses the diaphragm, wherein the pair of electrodes comprises a diaphragm head portion of each of the pair of electrodes positioned on, in, and/or near an exposed exterior surface of the diaphragm head, wherein when the first voltage potential is applied across the pair of electrodes for the first period of time the plasma is generated proximate the exposed exterior surface of the diaphragm head such that the plasma disinfects the exposed exterior surface of the diaphragm head.

7. The stethoscope according to claim 6, further comprising:
    a right ear tube and a left ear tube, wherein the right ear tube and the left ear tube are configured such that a proximal end of the right ear tube and a proximal end of the left ear tube are configured to be positioned proximate a user's ear so as to allow the user to hear vibrations corresponding to the movement generated by the patient; and
    a stem, wherein the stem interconnects the diaphragm head to the right ear tube and interconnects the diaphragm head to the left ear tube such that vibrations of the diaphragm due to movement generated by the patient travel via the stem to the right ear tube and the left ear tube, wherein the pair of electrodes comprises a stem portion of each of the pair of electrodes positioned on, in, and/or near an exposed exterior surface of the stem, wherein when the first voltage potential is applied across the pair of electrodes for the first period of time the plasma is generated proximate the exposed exterior surface of the stem such that the plasma disinfects the exposed exterior surface of the stem.

8. The stethoscope according to claim 7, wherein the pair of electrodes comprises a right ear tube portion and a left ear tube portion of each of the pair of electrodes positioned on, in, and/or near an exposed exterior surface of the right ear tube and an exposed exterior surface of the left ear tube, wherein when the first voltage potential is applied across the pair of electrodes for the first period of time the plasma is generated proximate the exposed exterior surface of the right ear tube and the exposed exterior surface of the left ear tube such that the plasma disinfects the exposed exterior surface of the right ear tube and the exposed exterior surface of the left ear tube.

9. The stethoscope according to claim 8, wherein an exposed exterior surface of the stethoscope comprises the exposed exterior surface of the diaphragm, the exposed exterior surface of the diaphragm head, the exposed exterior surface of the stem, the exposed exterior surface of the right ear tube, and the exposed exterior surface of the left ear tube, wherein when the first voltage potential is applied across the pair of electrodes for the first period of time the plasma generated proximate the exposed exterior surface of the stethoscope disinfects the entire exposed exterior surface of the stethoscope.

10. The stethoscope according to claim 1, wherein when the first voltage potential is applied across the pair of electrodes for a second period of time a plasma discharge is generated proximate the exposed exterior surface of the diaphragm such that the plasma sterilizes the exposed exterior surface of the diaphragm.

11. The stethoscope according to claim 10, further comprising:
    a diaphragm head, wherein the diaphragm head houses the diaphragm, wherein the pair of electrodes comprises a diaphragm head portion of each of the pair of electrodes positioned on, in, and/or near an exposed exterior surface of the diaphragm head, wherein when the first voltage potential is applied across the pair of electrodes for the second period of time the plasma is generated proximate the exposed exterior surface of the diaphragm head such that the plasma sterilizes the exposed exterior surface of the diaphragm head.

12. The stethoscope according to claim 11, further comprising:
    a right ear tube and a left ear tube, wherein the right ear tube and the left ear tube are configured such that a proximal end of the right ear tube and a proximal end of the left ear tube are configured to be positioned proximate a user's ear so as to allow the user to hear vibrations corresponding to the movement generated by the patient; and
    a stem, wherein the stem interconnects the diaphragm head to the right ear tube and interconnects the diaphragm head to the left ear tube such that vibrations of the diaphragm due to movement generated by the patient travel via the stem to the right ear tube and the left ear tube, wherein the pair of electrodes comprises a stem portion of each of the pair of electrodes positioned on, in, and/or near an exposed exterior surface of the stem, wherein when the first voltage potential is applied across the pair of electrodes for the second period of time the plasma is generated proximate the exposed exterior surface of the stem such that the plasma sterilizes the exposed exterior surface of the stem.

13. The stethoscope according to claim 12, wherein the pair of electrodes comprises a right ear tube portion and a left ear tube portion of each of the pair of electrodes positioned on, in, and/or near an exposed exterior surface of the right ear tube and an exposed exterior surface of the left ear tube, wherein when the first voltage potential is applied across the pair of electrodes for the second period of time the plasma is generated proximate the exposed exterior surface of the right ear tube and the exposed exterior surface of the left ear tube such that the plasma sterilizes the exposed exterior surface of the right ear tube and the exposed exterior surface of the left ear tube.

14. The stethoscope according to claim 13, wherein an exposed exterior surface of the stethoscope comprises the exposed exterior surface of the diaphragm, the exposed exterior surface of the diaphragm head, the exposed exterior surface of the stem, the exposed exterior surface of the right ear tube, and the exposed exterior surface of the left ear tube, wherein when the first voltage potential is applied across the pair of electrodes for the second period of time the plasma generated proximate the exposed exterior surface of the stethoscope sterilizes the entire exposed exterior surface of the stethoscope.

15. The stethoscope according to claim 1, wherein when a second voltage potential is applied across the pair of electrodes for a second period of time a plasma discharge is generated proximate the exposed exterior surface of the diaphragm such that the plasma sterilizes the exposed exterior surface of the diaphragm.

16. The stethoscope according to claim 15, further comprising:
a diaphragm head, wherein the diaphragm head houses the diaphragm, wherein the pair of electrodes comprises a diaphragm head portion of each of the pair of electrodes positioned on, in, and/or near an exposed exterior surface of the diaphragm head, wherein when the second voltage potential is applied across the pair of electrodes for the second period of time the plasma is generated proximate the exposed exterior surface of the diaphragm head such that the plasma sterilizes the exposed exterior surface of the diaphragm head.

17. The stethoscope according to claim 16, further comprising:
a right ear tube and a left ear tube, wherein the right ear tube and the left ear tube are configured such that a proximal end of the right ear tube and a proximal end of the left ear tube are configured to be positioned proximate a user's ear so as to allow the user to hear vibrations corresponding to the movement generated by the patient; and
a stem, wherein the stem interconnects the diaphragm head to the right ear tube and interconnects the diaphragm head to the left ear tube such that vibrations of the diaphragm due to movement generated by the patient travel via the stem to the right ear tube and the left ear tube, wherein the pair of electrodes comprises a stem portion of each of the pair of electrodes positioned on, in, and/or near an exposed exterior surface of the stem, wherein when the second voltage potential is applied across the pair of electrodes for the second period of time the plasma is generated proximate the exposed exterior surface of the stem such that the plasma sterilizes the exposed exterior surface of the stem.

18. The stethoscope according to claim 17, wherein the pair of electrodes comprises a right ear tube portion and a left ear tube portion of each of the pair of electrodes positioned on, in, and/or near an exposed exterior surface of the right ear tube and an exposed exterior surface of the left ear tube, wherein when the second voltage potential is applied across the pair of electrodes for the second period of time the plasma is generated proximate the exposed exterior surface of the right ear tube and the exposed exterior surface of the left ear tube such that the plasma sterilizes the exposed exterior surface of the right ear tube and the exposed exterior surface of the left ear tube.

19. The stethoscope according to claim 18, wherein an exposed exterior surface of the stethoscope comprises the exposed exterior surface of the diaphragm, the exposed exterior surface of the diaphragm head, the exposed exterior surface of the stem, the exposed exterior surface of the right ear tube, and the exposed exterior surface of the left ear tube, wherein when the second voltage potential is applied across the pair of electrodes for the second period of time the plasma generated proximate the exposed exterior surface of the stethoscope sterilizes the entire exposed exterior surface of the stethoscope.

* * * * *

UNITED STATES PATENT AND TRADEMARK OFFICE
CERTIFICATE OF CORRECTION

| | |
|---|---|
| PATENT NO. | : 9,056,148 B2 |
| APPLICATION NO. | : 13/881767 |
| DATED | : June 16, 2015 |
| INVENTOR(S) | : Karl R. Zawoy et al. |

It is certified that error appears in the above-identified patent and that said Letters Patent is hereby corrected as shown below:

In the specification,
Column 9,
Line 51, "LTV created" should read --UV created--.

Signed and Sealed this
Twenty-second Day of December, 2015

Michelle K. Lee
*Director of the United States Patent and Trademark Office*